United States Patent [19]

Ramert et al.

[11] Patent Number: 5,663,338
[45] Date of Patent: Sep. 2, 1997

[54] NEW PROCESS FOR PREPARING 2-AMINO-6-CHLOROPURINE

[75] Inventors: Reiner Ramert, Weiler bei Bingen; Rainer Sobotta, Ingelheim am Rhein, both of Germany

[73] Assignee: Boehringer Ingelheim KG, Ingelheim am Rhein, Germany

[21] Appl. No.: 632,704

[22] Filed: Apr. 15, 1996

[51] Int. Cl.$^6$ .......................... C07D 473/40; C07B 39/00
[52] U.S. Cl. ........................................................ 544/277
[58] Field of Search ................................................ 544/277

[56] References Cited

FOREIGN PATENT DOCUMENTS 5-213952  8/1993  Japan .

*Primary Examiner*—Mark L. Berch
*Attorney, Agent, or Firm*—Robert P. Raymond; Wendy E. Rieder; Alan R. Stempel

[57] ABSTRACT

The present invention relates to a new and improved process for preparing 2-amino-6-chloropurine comprising the step of reacting guanine in the presence of ammonium sulphate with hexamethyldisilazane. The process of this invention advantageously results in a high yield of 2-amino-6-chloropurine and may be carried out on a laboratory or an industrial scale.

4 Claims, No Drawings

NEW PROCESS FOR PREPARING 2-AMINO-6-CHLOROPURINE

TECHNICAL FIELD OF INVENTION

The present invention relates to a new and improved process for preparing 2-amino-6-chloropurine comprising the step of reacting guanine in the presence of ammonium sulphate with hexamethyldisilazane. The process of this invention advantageously results in a high yield of 2-amino-6-chloropurine and may be carried out on a laboratory or an industrial scale.

BACKGROUND OF THE INVENTION

2-Amino-6-chloropurine is an essential intermediate in the preparation of nucleoside-analogue pharmaceutical compositions which are effective antiviral agents, such as Pencyclovir and Famicyclovir.

Numerous methods of preparing such 2-amino-6-halopurines are already known from the prior art. Thus, British Patent 767216 describes a process in which guanine is first reacted with phosphorus pentasulphide, thereby introducing a mercapto group into the 6-position of the purine system. Subsequent treatment with chlorine leads to the corresponding 6-chloro derivative in the second step of the reaction.

However, this method of synthesis has the disadvantage, among others, that the decomposition products of phosphorus pentasulphide have an unpleasant odour, which necessarily involves the risk of undesirable environmental effects. Other disadvantages of this process arise from the low yield and from the fact that the thioguanine which is obtained in the first reaction step has been shown to have mutagenic properties. In another process, 2-amino-6-mercaptopurine is converted into the corresponding 6-thiomethyl derivative using methyl iodide; subsequent treatment with chlorine leads to the desired 6-chloro derivative, as in the process described above (J. Am. Chem. Soc. 79 (1957) 2185; J. Am. Chem. Soc. 82(1960) 2633), but this method of synthesis does not get around the disadvantages of the process described above.

In a fundamentally different method of production, guanine is reacted with phosphorus oxychloride in the presence of a quaternary ammonium salt, which is a direct method of producing the 2-amino-6-chloropurine (published Japanese Application No. 227583/1986). However, this procedure has the disadvantage that the yield is only in the range from 30 to 42%, owing to the dissolving characteristics of the guanine.

A more recent process (EP 0 543 095) describes a reaction route via a different type of intermediate product. Here, guanine is reacted in the presence of a halogenating agent with N,N-dialkylformyl compounds such as N,N-dimethylformamide, N,N-diethylformamide, N-methylformanilide, N,N-dimethylacetamide, N-formylpiperazine and N-formylmorpholine.

The subsequent hydrolysis makes it possible, by this method, to obtain 2-amino-6-chloropurine, inter alia, which should thus be accessible in a maximum yield of up to 70% on the basis of laboratory-scale experiments.

Another recently disclosed method of production starts from 2,9-diacetylguanine (WO 93/15075). Here, 2,9-diacetylguanine is reacted, inter alia, in the presence of a phase transfer catalyst, e.g. triethylmethylammonium chloride, with a chlorinating agent such as 2 to 4 equivalents of phosphorus oxychloride. Then, in the second reaction step, both acyl groups are hydrolytically cleaved using aqueous sodium hydroxide solution. Using this method, 2-amino-6-chloropurine can be obtained in a yield of about 75%.

Also recently disclosed was a process which starts from the guanine precursor 2,4-diamino-6-hydroxypyrimidine and proceeds, in a manner known per se, via the intermediate stages of 2,4-diamino-6-chloropyrimidine and 2,4-diamino-5-nitro-6-chloropyrimidine. The latter has to be catalytically hydrogenated and cyclised with a reactive formic acid derivative, such as an orthoester. This process has the particular disadvantage, compared with conventional guanine synthesis, that nitrogenation has to be carried out instead of nitrosation (DE OS 41 42 568).

In addition to the disadvantages mentioned above, the processes known from the prior art have another disadvantage, particularly affecting those processes which start with guanine, in that the unreacted guanine can only be removed at considerable expense.

SUMMARY OF THE INVENTION

The aim of the present invention is therefore to provide a process for preparing 2-amino-6-chloropurine which does not have the disadvantages known from the prior art and which largely does away with the need for laborious removal of unreacted guanine.

A further aim of the present invention is to provide a process for preparing 2-amino-6-chloropurine which is not only suitable for use on a laboratory scale but also makes it possible to produce 2-amino-6-chloropurine on an industrial scale.

These and other aims are accomplished by the process for preparing 2-amino-6-chloropurine according to this invention, which comprises as one of its key steps the reaction of guanine with hexamethyldisilazane in the presence of ammonium sulfate.

DETAILED DESCRIPTION OF THE INVENTION

The process of this invention for preparing 2-amino-6-chloropurine comprises the step of reacting guanine with hexamethyldisilazane in the presence of ammonium sulfate.

In a preferred embodiment, the process of this invention for preparing 2-amino-6-chloropurine comprises the steps of:

(a) reacting guanine with hexamethyldisilazane in the presence of ammonium sulphate;

(b) reacting the product from step (a) with an inorganic acid chloride;

(c) adding the product from step (b) to an aqueous alkaline solution;

(d) hydrolysing the reaction mixture produced in step (c); and (e) isolating 2-amino-6-chloropurine from the hydrolysed reaction mixture produced in step (d).

In other preferred embodiments, this process comprises the steps of reacting guanine in the presence of ammonium sulphate with hexamethyldisilazane in a polar solvent, preferably N,N-dimethylacetamide, at elevated temperature, preferably under reflux conditions, until a clear reaction mixture is obtained. The solvent and the unreacted hexamethyldisilazane are then distilled off under reduced pressure and the residue remaining is cooled, combined with an inorganic acid chloride—such as phosphorus pentachloride, phosphorus trichloride, thionyl chloride and preferably phosphorus oxychloride, and a solvent, preferably acetonitrile, and a phase transfer catalyst, preferably triethylbenzylammonium chloride, and reacted at elevated temperature, preferably under reflux conditions, whilst any low boiling reaction products such as trimethylchlorosilane are distilled off. Subsequently, the solvent and excess phosphorus oxychloride are distilled off under reduced pressure and the evaporation residue is added to an aqueous solution of an alkali metal hydroxide, preferably to dilute sodium or potassium hydroxide solution. The resulting reaction mixture is hydrolysed as completely as possible at a pH greater than 3, preferably in the range from 5 to 8 and most preferably in the range from 6 to 7, at elevated temperature, preferably boiling temperature, whilst any components of the reaction mixture which are volatile under these conditions are distilled off. After the hydrolysis mixture has been cooled, preferably to ambient temperature, and after seeding, if necessary, the 2-amino-6-chloropurine crystallises out in the form of yellowish crystals. After conventional isolation procedures, a 2-amino-6-chloropurine is thus obtained in good yields, containing less than one percent of unreacted guanine (HPLC).

A particularly preferred process for preparing 2-amino-6-chloropurine according to this invention comprises the steps of:

(a) reacting guanine with hexamethyldisilazane in the presence of ammonium sulphate in a solvent;

(b) removing the solvent and the unreacted hexamethyldisilazane from the reaction mixture produced in step (a) to produce a residue;

(c) combining the residue produced in step (b) with an inorganic acid chloride and a solvent;

(d) heating the reaction mixture produced in step (c) and distilling off the low boiling components to produce a residue;

(e) adding the residue produced in step (d) to an aqueous alkaline solution;

(f) hydrolysing the reaction mixture produced in step (e) at a pH of greater than about 3 at elevated temperature;

(g) distilling off the volatile components from the reaction mixture produced in step (f);

(h) cooling the solution produced in step (g); and (i) precipitating and isolating 2-amino-6chloropurine from the cooled solution produced in step (h).

A more preferred process for preparing 2-amino-6chloropurine according to this invention comprises the steps of:

(a) reacting guanine with hexamethyldisilazane in the presence of ammonium sulphate in a polar solvent at elevated temperature;

(b) distilling off the polar solvent and the unreacted hexamethyldisilazane from the reaction mixture produced in step (a) under reduced pressure to produce a residue;

(c) combining the residue produced in step (b) with phosphorus oxychloride and a phase transfer catalyst in a solvent;

(d) heating the reaction mixture produced in step (c), distilling off the low boiling components, distilling off the solvent from step (c) and excess phosphorus oxychloride under reduced pressure to produce a residue;

(e) adding the residue produced in step (d) to an aqueous solution of an alkali metal hydroxide;

(f) hydrolysing the reaction mixture produced in step (e) at a pH in the range from about 5 to about 8 at elevated temperature;

(g) distilling off the volatile components from the reaction mixture produced in step (f);

(h) cooling the solution produced in step (g); and (i) precipitating and isolating 2-amino-6-chloropurine from the cooled solution produced in step (h).

The most preferred process for preparing 2-amino-6-chloropurine according to this invention comprises the steps of:

(a) reacting guanine with hexamethyldisilazane in the presence of ammonium sulphate in N,N-dimethylacetamide under reflux conditions;

(b) distilling off the N,N-dimethylacetamide and the unreacted hexamethyldisilazane from the reaction mixture produced in step (a) under reduced pressure to produce a residue;

(c) combining the residue produced in step (b) with phosphorus oxychloride, acetonitrile and triethylbenzyl-ammonium chloride;

(d) heating the reaction mixture produced in step (c) to reflux temperature, distilling off the low boiling components and distilling off the acetonitrile and excess phosphorus oxychloride under reduced pressure to produce a residue;

(e) adding the residue produced in step (d) to an aqueous sodium or potassium hydroxide solution;

(f) hydrolyzing the reaction mixture produced in step (e) at a pH in the range from about 6 to about 7 at boiling temperature;

(g) distilling off the volatile components from the reaction mixture produced in step (f);

(h) cooling the solution produced in step (g); and (i) precipitating and isolating 2-amino-6-chloropurine from the cooled solution produced in step (h).

The objectives described above are achieved by means of the processes outlined above and further illustrated in the Examples. Various other embodiments of the process will be apparent to anyone skilled in the art from the descriptions provided. However, it is expressly pointed out that the Examples and the associated description are provided purely as an exemplification and illustration and should not be regarded as restricting the invention.

EXAMPLES

Example 1

121 g (0.8 mol) of guanine and 1.6 g of ammonium sulphate were suspended in 800 ml of N,N-dimethylacetamide, 864 ml of hexamethyldisilazane were added and the mixture was refluxed for 4 hours. Excess hexamethyldisilazane and the solvent were distilled off in vacuo. The residue was combined with 450 ml of phosphorus oxychloride, 280 g of triethylbenzylammonium chloride and 320 ml of acetonitrile and boiled for about 1 hours, whilst any low boiling fractions, predominantly trimethylchlorosilane, were distilled off through a short Vigreux column. Then the solvent and excess phosphorus oxychloride were distilled off under reduced pressure and the evaporation residue was added dropwise without cooling to a supply of sodium hydroxide solution. The hot solution was boiled at pH 6–7 in order to complete the hydrolysis, during which organic components were distilled off. Then it was cooled, seeded (if necessary) and left to crystallise at ambient temperature for a period of about 12 hours. The precipitate was suction filtered, washed thoroughly with water and dried. 108 g (79.8% of theory) of yellowish crystals of 2-amino-6-chloropurine were obtained, with a guanine content (HPLC) of 0.2–0.3%.

Example 2

30.3 kg (200 mol) of guanine, 0.4 kg of ammonium sulphate, 235 kg of N,N-dimethylacetamide and 211 kg of hexamethyldisilazane were refluxed in a 500 litre enamel stirring apparatus until a clear solution was obtained. Excess hexamethylsilazane and the solvent were distilled off completely with the gradual application of vacuum. 113 liters of phosphorus oxychloride were carefully added to the residue, then 80 liters of acetonitrile and 70 kg of triethylbenzylammonium chloride were added and the mixture was brought to the boil again. After about 1 hour when about 65 liters had been distilled off, distillation was continued with gradual lowering of the pressure until a viscous residue was obtained.

This was added slowly and with cooling to 900 liters of 13% potassium hydroxide solution which had been placed in a 1200 liter enamel stirring apparatus. The solution was neutralised, heated to boiling whilst the pH was monitored and distilled until a sump temperature of 100° C. was achieved. After cooling and, seeding the product was stirred until it had crystallised out completely, the crystals were then centrifuged, washed and dried. 30.6 kg (90.5% of theory) of ochre-coloured finely crystalline 2-amino-6-chloropurine were obtained with a guanine content (HPLC) of about 0.9%.

We claim:

1. A process for preparing 2-amino-6-chloropurine, comprising the steps of:
   (a) reacting guanine with hexamethyldisilazane in the presence of ammonium sulphate;
   (b) reacting the product from step (a) with an inorganic acid chloride;
   (c) adding the product from step (b) to an aqueous alkaline solution;
   (d) hydrolysing the reaction mixture produced in step (c); and
   (e) isolating 2-amino-6-chloropurine from the hydrolysed reaction mixture produced in step (d).

2. A process for preparing 2-amino-6-chloropurine, comprising the steps of:
   (a) reacting guanine with hexamethyldisilazane in the presence of ammonium sulphate in a solvent;
   (b) removing the solvent and the unreacted hexamethyldisilazane from the reaction mixture produced in step (a) to produce a residue;
   (c) combining the residue produced in step (b) with an inorganic acid chloride and a solvent;
   (d) heating the reaction mixture produced in step (c) and distilling off the low boiling components to produce a residue;
   (e) adding the residue produced in step (d) to an aqueous alkaline solution;
   (f) hydrolysing the reaction mixture produced in step (e) at a pH of greater than about 3 at elevated temperature;
   (g) distilling off the volatile components from the reaction mixture produced in step (f);
   (h) cooling the solution produced in step (g); and
   (i) precipitating and isolating 2-amino-6-chloropurine from the cooled solution produced in step (h).

3. The process according to claim 2, comprising the steps of:
   (a) reacting guanine with hexamethyldisilazane in the presence of ammonium sulphate in a polar solvent at elevated temperature;
   (b) distilling off the polar solvent and the unreacted hexamethyldisilazane from the reaction mixture produced in step (a) under reduced pressure to produce a residue;
   (c) combining the residue produced in step (b) with phosphorus oxychloride and a phase transfer catalyst in a solvent;
   (d) heating the reaction mixture produced in step (c), distilling off the low boiling components, distilling off the solvent from step (c) and excess phosphorus oxychloride under reduced pressure to produce a residue;
   (e) adding the residue produced in step (d) to an aqueous solution of an alkali metal hydroxide;
   (f) hydrolysing the reaction mixture produced in step (e) at a pH in the range from about 5 to about 8 at elevated temperature;
   (g) distilling off the volatile components from the reaction mixture produced in step (f);
   (h) cooling the solution produced in step (g); and
   (i) precipitating and isolating 2-amino-6-chloropurine from the cooled solution produced in step (h).

4. The process according to claim 3, comprising the steps of:
   (a) reacting guanine with hexamethyldisilazane in the presence of ammonium sulphate in N,N-dimethylacetamide under reflux conditions;
   (b) distilling off the N,N-dimethylacetamide and the unreacted hexamethyldisilazane from the reaction mixture produced in step (a) under reduced pressure to produce a residue;
   (c) combining the residue produced in step (b) with phosphorus oxychloride, acetonitrile and triethylbenzyl-ammonium chloride;
   (d) heating the reaction mixture produced in step (c) to reflux temperature, distilling off the low boiling components and distilling off the acetonitrile and excess phosphorus oxychloride under reduced pressure to produce a residue;
   (e) adding the residue produced in step (d) to an aqueous sodium or potassium hydroxide solution;
   (f) hydrolyzing the reaction mixture produced in step (e) at a pH in the range from about 6 to about 7 at boiling temperature;
   (g) distilling off the volatile components from the reaction mixture produced in step (f);
   (h) cooling the solution produced in step (g); and
   (i) precipitating and isolating 2-amino-6-chloropurine from the cooled solution produced in step (h).

* * * * *